(12) United States Patent
Jones et al.

(10) Patent No.: US 6,552,231 B2
(45) Date of Patent: Apr. 22, 2003

(54) METHOD FOR MAKING DIMETHYL SULFONE FROM DIMETHYL SULFOXIDE AND HYDROGEN PEROXIDE

(75) Inventors: Charles A. Jones, Warrior, AL (US); Joyce D. Friedrich, Gardendale, AL (US); John C. Paschall, Ozark, AL (US); Wima K. Alwis, Homewood, AL (US)

(73) Assignee: Sloss Industries Corporation, Birmingham, AL (US)

( * ) Notice: Subject to any disclaimer, the term of this patent is extended or adjusted under 35 U.S.C. 154(b) by 0 days.

(21) Appl. No.: 09/897,374

(22) Filed: Jul. 2, 2001

(65) Prior Publication Data

US 2002/0004614 A1 Jan. 10, 2002

Related U.S. Application Data

(60) Provisional application No. 60/215,961, filed on Jul. 5, 2000.

(51) Int. Cl.⁷ ............................................. C07C 315/02
(52) U.S. Cl. ......................................................... 568/28
(58) Field of Search ........................................... 568/28

(56) References Cited

U.S. PATENT DOCUMENTS 3,006,963 A * 10/1961 Buc et al.
3,069,471 A * 12/1962 Tashlick
3,849,499 A * 11/1974 Malievsky et al.
4,097,526 A *  6/1978 Chan

OTHER PUBLICATIONS

132:194029 abs of Analele Stiintifice ale Universitatii "Al. I. Cuza" din Iasi, Chimie by Hulea et al 6, pp137–144 1998.*

* cited by examiner

Primary Examiner—Jean F. Vollano
(74) Attorney, Agent, or Firm—McDonnell Boehnen Hulbert & Berghoff

(57) ABSTRACT

The present invention provides a process for synthesizing dimethyl sulfone by the oxidation of dimethyl sulfoxide with hydrogen peroxide.

14 Claims, 1 Drawing Sheet

METHOD FOR MAKING DIMETHYL SULFONE FROM DIMETHYL SULFOXIDE AND HYDROGEN PEROXIDE

BACKGROUND OF THE INVENTION a) Field of the Invention

The present invention pertains to a method for making dimethyl sulfone from dimethyl sulfoxide and hydrogen peroxide. The application claims the priority of Provisional Application Ser. No. 60/215,961, filed Jul. 5, 2000.

b) Description of the Related Art

Dimethyl sulfone (also known as methylsulfonylmethane, MSM, and $DMSO_2$), the oxidized form of dimethyl sulfoxide, is a well-known natural health product (Jacob, S. W.; Lawrence, R. M.; Zucker, M. *The Miracle of MSM,* New York: Berkley Books, 1999). Its uses have been described in several patents, including as a dietary sulfur supplement (U.S. Pat. No. 4,616,039), as a treatment for parasite infections (U.S. Pat. No. 4,914,135), as a pharmaceutical carrier (U.S. Pat. No. 4,468,547), and as a food additive (U.S. Pat. No. 5,071,878).

Known processes for the preparation of dimethyl sulfone from dimethyl sulfoxide utilize assorted catalysts, including a molybdate catalyst in the presence of sulfuric acid. The process requires the use of glass-lined reactors, the neutralization of acid components, and the caustic decomposition of hydrogen peroxide prior to product isolation and, therefore, results in the generation of salt by-products. Isolation of the dimethyl sulfone requires high vacuum and high temperature. The final product is flaked to obtain a flowing solid material.

U.S. Pat. No. 3,069,471 describes a process for preparing sulfones by the slow addition of hydrogen peroxide to the corresponding sulfoxide. Although this method avoids catalysts and organic solvents, it produces small amounts of acidic by-products. In addition, the process requires close monitoring of the hydrogen peroxide concentrations and the amount of water present in the reaction vessel in order to avoid explosive decomposition of the hydrogen peroxide.

Japanese Patent 79 44,611 similarly describes the production of dimethyl sulfone and is subject to the same limitations as U.S. Pat. No. 3,069,471.

Because dimethyl sulfone is used as a health product, it is desirable to have a process for making the material in pure form without the use of added catalyst and which results in limited or no by-product formation.

BRIEF SUMMARY OF THE INVENTION

The present invention provides a process for preparing dimethyl sulfone by the oxidation of dimethyl sulfoxide using hydrogen peroxide, without the necessity of added catalysts. The process also accommodates the use of naturally-derived dimethyl sulfoxide from pine tree process and dimethyl sulfoxide derived from petroleum sources such as sour gas wells. The process comprises the steps of: a) simultaneously adding dimethyl sulfoxide and an aqueous solution of hydrogen peroxide to a pre-heated heel of aqueous dimethyl sulfone in the smaller of two reaction vessels at a rate sufficient to maintain the reactor at or below 120° C. during the exothermic reaction; b) transferring the partially-reacted mixture into a larger reaction vessel where the reaction is completed by the continued simultaneous charging of the raw materials; c) distilling water from the mixture contained in the larger reactor during the reaction; and d) isolation of the final product as either a free-flowing, crystallized solid by filtration or centrifugation or as a flaked solid by distillation and flaking.

It is an object of this invention to provide pure, crystalline (or flaked), flowable dimethyl sulfone suitable for administration to humans.

DETAILED DESCRIPTION OF THE INVENTION

Figure 1:
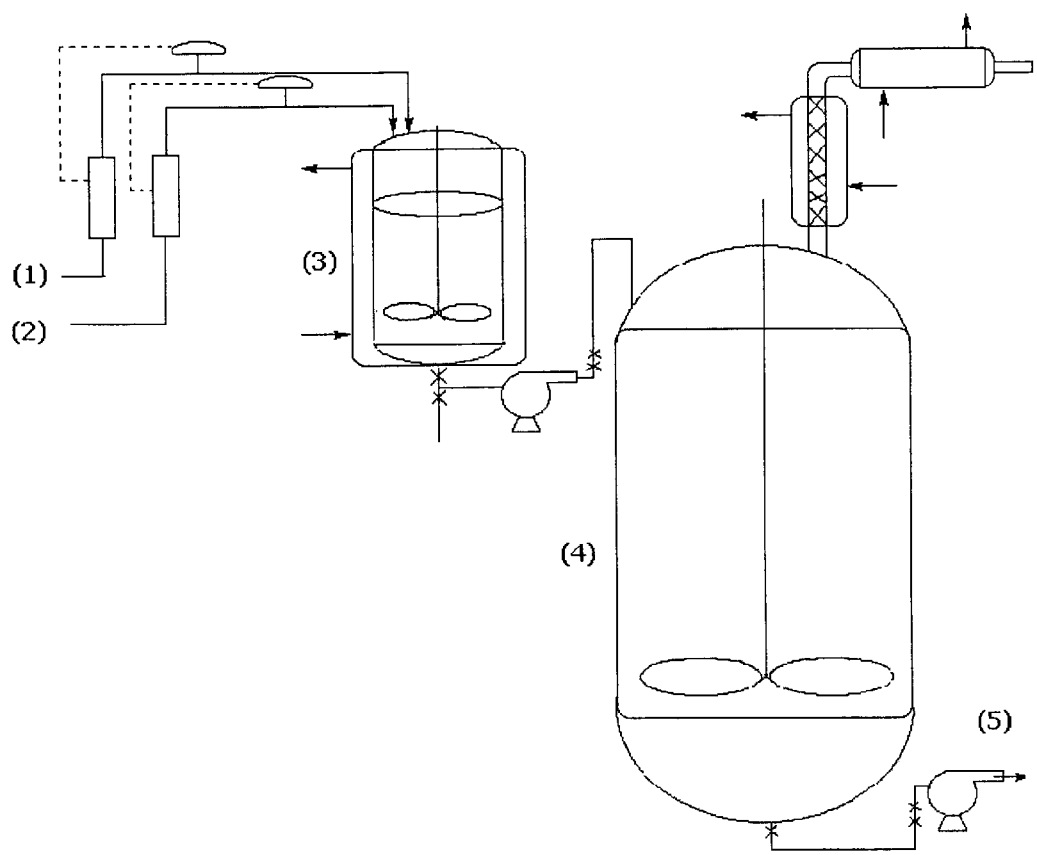
FIG. 1 is a schematic representation of the process equipment utilized in the present invention.

Currently, dimethyl sulfone is produced on the plant scale by the oxidation of dimethyl sulfoxide with 50% hydrogen peroxide in the presence of a molybdate/sulfuric acid catalyst. Significant disadvantages of this process include the following. Acids accelerate the thermal decomposition of dimethyl sulfoxide (Head and McCarty, *Tet. Lett.,* (16), 1405–1408 (1973). A separate step is required to neutralize these acid components. Excess hydrogen peroxide is removed by caustic decomposition prior to distillation of the product. The process necessitates the complete removal of water from the system by distillation. The process generates salt by-products. The final product distillation requires high vacuum and high temperatures. The final product must be flaked to obtain a flowing solid material.

The present invention provides a number of significant advantages over the existing procedure. The invention does not require an added catalyst and allows for the simultaneous addition of raw materials into the reaction vessel, which may be constructed of stainless steel. Because the raw materials are simultaneously added, overheating of the dimethyl sulfoxide and production of acidic by-products are minimized. The exotherm can also be controlled by the feed rate of one or both of the raw materials. Further control of the exotherm is provided by the dilution of the reaction mixture by a previously charged heel of aqueous dimethyl sulfone. Higher throughput yields are maintained by initially generating the required heel for the larger reactor in the smaller vessel. Due to its diminished size, the smaller reactor only demands the use of a nominal heel of sulfone generated elsewhere. Transferring of the contents of the smaller reactor to the larger vessel thus safely provides the necessary heel for the primary reaction. The process only requires partial removal of in-process water during production. In-process monitoring of unreacted dimethyl sulfoxide and residual hydrogen peroxide can be performed by gas chromatography and iodometric titration, respectively. Because there is no added catalyst, stainless steel reactors may be substituted for glass-lined reactors and neutralization of the acid is not required nor is salt formation a factor. Unless the final product is distilled, caustic decomposition of any excess hydrogen peroxide is not mandatory. The product may be recrystallized from water or ethanol, thus eliminating the high vacuum and excessive temperatures necessary during the typical isolation of dimethyl sulfone by distillation. The recrystallized product is easily dried under vacuum at 60–75° C. to yield a white, free-flowing, crystalline material, without the necessity of flaking.

The process of the present invention is performed in a process unit as depicted schematically in FIG. 1, which is comprised of a smaller primary reaction vessel (3), containing an adequate heel of aqueous dimethyl sulfone; means with adjustable valves for simultaneously adding the reactants at the desired rate (1) and (2); temperature monitoring devices; a larger secondary reaction vessel (4); means for removing water by distillation; means for heating and/or cooling the reaction vessels; and means for transferring materials from one site to another during the process.

Hydrogen peroxide and dimethyl sulfoxide, (1) and (2), are simultaneously fed into the precharged and preheated primary reactor (3) in the proper proportions and at a predetermined rate. After the appropriate hold time, the partially reacted mixture is then transferred from the smaller reactor into the larger reactor (4) where the reaction is completed by the continued simultaneous charging of the raw materials as water is distilled from the reaction mixture. Upon completion of the reaction, the mixture is directed to either the recrystallization vessel and ultimately to the centrifuge or to the distillation vessel, as required (5).

The preferred embodiment of the process utilizes 1–1.5 moles of hydrogen peroxide, preferably 1.2 moles, for every mole of methyl sulfoxide. Hydrogen peroxide is delivered as a 30–70% aqueous solution, preferably 50%. The primary and secondary flasks are preheated to between about 70–120° C., preferably 95° C., prior to the addition of the raw materials. The reaction is monitored for consumption of dimethyl sulfoxide by chromatography, preferably gas chromatography.

The following example serves to illustrate the invention.

EXAMPLE 1

100 parts of dimethyl sulfoxide and 110 parts of 50% aqueous hydrogen peroxide (about 1.2 moles of hydrogen peroxide per mole of dimethyl sulfoxide) are simultaneously charged to a small, preheated (approximately 85–95° C.) reaction vessel equipped with two addition funnels and a thermowell and containing an adequate heel of aqueous dimethyl sulfone (approximately 60% by weight). Feed rates are controlled such that the reactor temperature does not exceed 120° C. during the exotherm. Cooling of the reactor may also be required. When a sufficient quantity of dimethyl sulfone has been generated to serve as the heel in the secondary, larger reactor, the flow of raw materials is discontinued. The contents of the smaller reactor are then held until the reaction temperature drops dramatically. At this is point, the warm contents may be transferred into the larger, secondary reactor, equipped with a thermowell and stillhead. The reaction mixture is heated to the aforementioned 85–95° C., if necessary. Raw materials are then simultaneously charged into the secondary reactor as previously prescribed. A second exotherm may be observed. Water is distilled from the reactor during the course of the reaction (approximately 50% of the total in the system). Upon completion of the reaction less than 1% dimethyl sulfoxide, as determined by gas chromatography, remained. Two distinct isolation methods are available according to the desired product characteristics:

a) Distilled and Flaked Dimethyl Sulfone

Further distillation of the completed reaction mixture requires basic decomposition of any residual hydrogen peroxide with 10% aqueous caustic. After the mixture is cooled to below 80° C., the pH is cautiously adjusted to between 8 and 9. Water and forerun are distilled from the mixture at atmospheric pressure. Vacuum (at least 40 mm Hg, followed by 20–30 mm Hg) is then applied and the final product is distilled as a colorless oil at approximately 160–175° C. The yield is typically $\geq$90%. The molten solid may then be cooled and flaked to produce a flowable material.

b) Recrystallized and Filtered or Centrifuged Dimethyl Sulfone

A volume of water equal to that of the distillate is returned to the reactor. The reaction contents are heated to redissolve any precipitated product and the solution is filtered while hot. The filtrate is allowed to cool to room temperature and then is chilled to 2° C. to 25° C., preferably 5° C., to crystallize out the desired product. The dimethyl sulfone is then isolated by vacuum filtration or centrifugation and is washed with a minimum of ice cold water. The white, crystalline, free-flowing solid is dried under vacuum at 25° C. to 80° C., preferably 70° C. Yield is typically $\geq$80%. When it is considered desirable, the product can be recrystallized from ethanol.

The above examples illustrate the present invention and are not intended to limit it in spirit or scope.

What is claimed is:

1. A method for making crystalline dimethyl sulfone comprising:
   (a) simultaneously adding dimethyl sulfoxide and an aqueous solution of hydrogen peroxide to a preheated, stainless steel reaction vessel precharged with an aqueous solution of dimethyl sulfone wherein the dimethyl sulfone and aqueous solution of hydrogen peroxide is added at a rate sufficient to maintain the reaction temperature below about 120° C.
   (b) distilling water from the reaction mixture;
   (c) then adding water to the reaction mixture to form a dilute reaction solution;
   (d) heating and filtering the heated dilute reaction solution;
   (e) cooling the dilute reaction solution to crystallize out the dimethyl sulfone; and
   (f) filtering or centrifuging the crystallized dimethyl sulfone.

2. The method according to claim 1 wherein the aqueous hydrogen peroxide solution is at a concentration between 40 and 60% of hydrogen peroxide.

3. The method according to claim 1 wherein the molar ratio of hydrogen peroxide to dimethyl sulfoxide is about 1.2.

4. The method according to claim 1 wherein the water distilled from the system during the course of the reaction is approximately 50% of the total system.

5. The method according to claim 1 wherein the water added to the reaction is about equal to the water removed from the reaction by distillation.

6. The method according to claim 1 wherein the reaction solution is cooled to about 2° C. to 25° C. to crystallize out the dimethyl sulfone.

7. The method according to claim 6 wherein the reaction solution is cooled to about 5° C. to crystallize out the dimethyl sulfone.

8. The method according to claim 1 wherein the filtered or centrifuged dimethyl sulfone is washed with ice cold water and dried under vacuum between about 25° C. and 80° C.

9. The method according to claim 8 wherein the filtered or centrifuged dimethyl sulfone is washed with ice cold water and dried under vacuum between about 60° C. and 70° C.

10. A method for making flaked dimethyl sulfone comprising:
   (a) simultaneously adding dimethyl sulfoxide and an aqueous solution of hydrogen peroxide to a preheated, stainless steel reaction vessel precharged with an aqueous solution of dimethyl sulfone at a rate sufficient to maintain the reaction temperature below about 120° C.;

(b) distilling water from the reaction mixture;

(c) cooling the reaction mixture to below 80° C.;

(d) adjusting the pH of the reaction mixture to about between 8 and 9 with aqueous caustic;

(e) distilling water from the reaction mixture at atmospheric pressure followed by distilling at a vacuum of at least 40 mm Hg and then followed by distilling at a vaccum of 20–30 mm Hg to provide a concentrated reaction mixture, (f) distilling dimethyl sulfone from the concentrated reaction mixture at about 160–175° C. as a colorless oil that solidifies upon cooling; and (g) flaking the dimethyl sulfone to provide a flowable dimethyl sulfone.

11. The method according to claim 10 wherein the vessel and a heel of aqueous solution of dimethyl sulfoxide are pre-heated to between about 70° C. and 120° C.

12. The method according to claim 10 wherein the aqueous hydrogen peroxide solution is at a concentration between 40 and 60%.

13. The method according to claim 10 wherein the molar ratio of hydrogen peroxide to dimethyl sulfoxide is about 1.2.

14. The method according to claim 10 wherein the pH of the reaction mixture is cautiously adjusted to about between 8 and 9 with 10% aqueous caustic.

* * * * *